(12) United States Patent
Whitson (10) Patent No.: US 8,454,980 B2
(45) Date of Patent: Jun. 4, 2013

(54) HYDROGEL BIOSCAFFOLD AND COATING FOR BONE AND TOOTH REPAIR

(76) Inventor: Stanley William Whitson, St. Louis, MO (US)

( * ) Notice: Subject to any disclaimer, the term of this patent is extended or adjusted under 35 U.S.C. 154(b) by 0 days.

(21) Appl. No.: 13/359,209

(22) Filed: Jan. 26, 2012

(65) Prior Publication Data

US 2012/0189668 A1 Jul. 26, 2012

Related U.S. Application Data

(60) Provisional application No. 61/436,357, filed on Jan. 26, 2011.

(51) Int. Cl.
*A61K 9/00* (2006.01)

(52) U.S. Cl.
USPC ......... 424/400; 514/15.2; 514/13.6; 424/641; 424/602

(58) Field of Classification Search
None
See application file for complete search history.

(56) References Cited

U.S. PATENT DOCUMENTS

| | | | |
|---|---|---|---|
| 5,583,114 A | 12/1996 | Barrows et al. | |
| 5,885,829 A | 3/1999 | Mooney et al. | |
| 6,258,778 B1 | 7/2001 | Rodgers et al. | |
| 6,599,515 B1 * | 7/2003 | Delmotte | 424/422 |
| 7,163,691 B2 | 1/2007 | Knaack et al. | |
| 2009/0232784 A1 | 9/2009 | Feldman et al. | |
| 2010/0216708 A1 | 8/2010 | Jacobs et al. | |

FOREIGN PATENT DOCUMENTS

| | | | |
|---|---|---|---|
| EP | 1719543 A1 | * | 11/2006 |
| WO | WO2008015475 | | 2/2008 |

OTHER PUBLICATIONS

"Protein-polymer conjugates for forming photopolymerizable biomimetic hydrogels for tissue engineering," Gonen-Wadmany, M., et al., Biomaterials 28: 3876-3886 (2007).*
Kanczler et al., Osteogenesis and Angiogenesis: The Potential for Engineering Bone, European Cells and Materials vol. 15, 2008, pp. 100-114.
Rompen et al., Kinetic Aspects of Gingival and Perodontal Ligament Fibroblast Attachment to Surface-Conditioned Dentin, J Dent Res, Mar. 1993, 72(3) pp. 607-612 Abstract.
Nakashima, M. (2005), Tissue Engineering in Endodontics. Australian Endodontic Journal, 31: 111-113 Abstract.
International Search Report and Written Opinion for International Application No. PCT/US2012/022744 dated Apr. 16, 2012.

* cited by examiner

*Primary Examiner* — David J Blanchard
*Assistant Examiner* — Daniel F Coughlin
(74) *Attorney, Agent, or Firm* — Polsinelli PC

(57) ABSTRACT

Hydrogel compositions that include an albumin/N-acetyl cysteine solution and an aqueous suspension of calcium salts or mixture of calcium and magnesium salts are described. Also described are methods of producing and using the hydrogel compositions as a support scaffold for mineralizing connective tissue replacement and repair.

18 Claims, 4 Drawing Sheets

HYDROGEL BIOSCAFFOLD AND COATING FOR BONE AND TOOTH REPAIR

CROSS REFERENCE TO RELATED APPLICATION

This application claims priority from U.S. provisional patent application Ser. No. 61/436,357, entitled "Hydrogel Bioscaffold and Coating for Bone and Tooth Repair" filed on Jan. 26, 2011, which is hereby incorporated by reference in its entirety.

FIELD

The present document generally relates to bio-resorbable, biologically-based hydrogels, and in particular to hydrogels that may serve as scaffolds for tissue regeneration or as non-toxic coatings for dental and surgical applications.

BACKGROUND

Using tissue engineering technology, mineralized connective tissues such as bone, cartilage, or dental pulp may be repaired or regenerated using a combination of living cells, engineered materials, and biochemical and physio-chemical factors. An engineered connective tissue may be grown in vitro on a matrix material in a culture seeded with connective tissue progenitor cells, such as stem cells. Alternatively, the matrix material may be inserted into an organism in a location where the connective tissue is needed, such as within an area of injured bone tissue, and the surrounding cells may infiltrate and attach to the matrix to form mineralized connective tissue.

A key element of the formation of these engineered tissues is the composition of matrix material, which acts as a physical support for the attachment and development of the connective tissue cells. To date, materials such as polyglycolic acid, combinations of polyglycolic acid and polylactic acid, polyethylene glycol, chitosan, and alginate have been used with limited success as scaffolds in bone, cartilage or dental pulp regeneration. Typically, only a relatively small fraction of the progenitor cells seeded into these existing matrix materials survives the initial contact with the matrix material, possibly because the progenitor cells of mineralized connective tissues are highly sensitive to the surrounding chemical environment, including the particular molecules forming the exposed surface of the matrix material.

As such, there exists a need for an improved matrix material capable of providing a physical support for the attachment and growth of mineralizing connective tissue progenitor cells, in which the matrix material incorporates molecules associated with typical connective tissue biology growth or repair. Such a matrix material may be used for dental pulp, bone and periodontium repair as well as for the formation of bioengineered bone tissue for transplant.

SUMMARY

In one aspect, a hydrogel composition for use as a support scaffold for developing mineralizing connective tissue is provided. The basic hydrogel solution consists of a 30% (w/v) solution of albumin in phosphate-buffered saline containing 40 mM N-acetylcysteine mixed in a 1:1 ratio with a suspension of mineral salt(s) in water. Either of two mineral salt suspensions stimulates hydrogel formation and alters the characteristics of the gel: (1) 0.5 g calcium hydroxide suspended in 10 mL water or (2) 0.5 g calcium hydroxide suspended in 10 mL water and 0.5 g magnesium hydroxide suspended in 10 mL water, then combined in ratios of 2.5:1 up to 6:1 calcium hydroxide to magnesium hydroxide. The albumin/N-acetylcysteine solution is mixed 1:1 with either of the mineral salt solutions, yielding a final volume ratio of (1) 1:1 for the albumin/N-acetylcysteine to calcium hydroxide mixture or (2) multiple volume ratios of albumin/N-acetylcysteine to the combined calcium hydroxide/magnesium hydroxide suspension. The addition of small amounts of other additives (e.g., fibrinogen, beta-glycerol phosphate, 2-phosphoascorbic acid) does not affect formation of the hydrogel.

In another aspect, a hydrogel composition for use as a coating for a bone or tooth implant is provided. The basic hydrogel composition includes an albumin solution containing about 30% (w/v) of albumin in a phosphate buffer and fibrinogen in an amount ranging from about 0.1 mg/mL to about 1.0 mg/mL, as well as an aqueous suspension containing about 0.5 mg of calcium hydroxide per 10 mL of water. The ratio of the albumin solution volume and the aqueous suspension ranges from about 1:1 to about 1:2.5. The hydrogel composition is formulated to promote osseointegration around a coated bone and/or tooth implant.

In an additional aspect, a hydrogel composition for use as a sealant for exposed dentin is provided. The hydrogel composition includes an albumin solution containing about 30% (w/v) of albumin in a phosphate buffer, N-acetylcysteine in an amount ranging from about 10 mM to about 40 mM, and 2-phosphoascorbic acid in an amount ranging from about 25 μg/mL to about 50 μg/mL. In addition, the hydrogel composition contains an aqueous suspension containing about 0.5 mg of calcium hydroxide per 10 mL of water. The ratio of the albumin solution volume and the aqueous suspension ranges from about 1:1 to about 1:2.5. The hydrogel composition is formulated to inhibit bacterial growth on the sealed dentin surface.

In another additional aspect, a method of producing a hydrogel composition for use as a support scaffold for developing mineralizing connective tissue is provided. The method includes mixing an albumin solution and an aqueous suspension at a ratio from 1:1 to about 1:2.5 albumin solution:aqueous suspension. The albumin solution includes about 30% (w/v) of albumin in a phosphate buffer, and the aqueous suspension comprises about 0.5 mg of calcium hydroxide per 10 mL of water.

Additional objectives, advantages and novel features will be set forth in the description which follows or will become apparent to those skilled in the art upon examination of the drawings and detailed description which follows.

BRIEF DESCRIPTION OF THE ILLUSTRATIONS

Corresponding reference characters and labels indicate corresponding elements among the views of the drawings. The headings used in the figures should not be interpreted to limit the scope of the claims.

DETAILED DESCRIPTION

Aspects of the invention provide bio-resorbable, biologically-based hydrogel materials, as well as methods of making the hydrogel materials. The hydrogel material may function as a scaffold for the development of engineered tissues by providing a substrate for angiogenesis and mineralized tissue formation. Alternatively, the hydrogel may function as a non-toxic coating that encourages the adhesion and proliferation of mineralizing connective tissue cells. The hydrogel material may include compounds associated with the growth, function, and maintenance of mineralizing connective tissue cells, such as albumin, fibrinogen, N-acetylcysteine, ascorbic acid, calcium salts, and magnesium salts.

The methods of making hydrogels, in particular the formulation of the ingredients combined to produce the hydrogel, can and will vary depending on the desired application or use of the resulting hydrogel. In general, the formulation of a hydrogel may be based on at least one or more criteria including, but not limited to making the gel conducive to the growth, function, and maintenance of mineralizing connective tissue cells, while providing a working time prior to gelation that provides sufficient time for the injection of the freshly mixed formulation of the hydrogel. In addition, the formulations may also vary depending on other desired properties of the hydrogel, including potential tensile strength, hardness and speed of resorption of the hydrogel.

Variations in the types and amounts of compounds included in the hydrogel as well as variations in the preparation procedures of the hydrogel may result in a variety of hydrogel forms. Non-limiting examples of suitable forms of the hydrogel produced by the method include: an interconnected porous form that may promote cell attachment and angiogenesis; a relatively non-porous form that may function as a physical barrier to unwanted epithelial and connective tissue downgrowth into bone or dental implants; a thin, less viscous non-porous form that may function as a tooth sealant/protectant for exposed dentin; a porous coating form for bone and tooth implants that may optimize osseointegration; and an injectable form that may be mixed with one or more growth factors, antibodies to mineralized tissue inhibitors and/or pathogens such as bacteria or fungi, and antibiotics to act as a biological glue to initially bind severely broken bones together.

A detailed description of various aspects of the hydrogel and methods of producing the hydrogel are provided below.

I. Composition of the Hydrogel

The composition of the hydrogel may incorporate compounds typically associated with the growth, repair and maintenance of mineralized connective tissues. The hydrogel may include albumin and fibrinogen, which are two key proteins present in the extracellular fluid that continuously bathes mineralizing connective tissue cells in vivo. Both albumin and fibrinogen may provide a bacteriostatic function by coating miniature channels such as the canaliculi within bone matrix and the tubules within dentin, thereby limiting the invasion of biofilm-forming bacteria. In addition, the fibrinogen may also provide binding sites to which reparative connective tissue cells may adhere.

In one aspect, two proteins, albumin and fibrinogen, are combined with two antioxidants, N-acetylcysteine and 2-phosphoascorbic acid, as well as an organic phosphate source, beta-glycerol phosphate. The antioxidants and the phosphate source may dampen inflammation at the application site of the hydrogel and may further promote mineralized tissue differentiation.

In addition, calcium hydroxide may be included in the composition as a gelation catalyst. However, due to the high pH of the calcium hydroxide, other composition ingredients may be included to achieve comparable gelation with relatively less calcium hydroxide in the composition. For example, the N-acetylcysteine may function as a catalyst for gelation, thus offsetting the amount of calcium hydroxide included in the formulation and the high, sustained pH that accompanies the inclusion of calcium hydroxide. The deleterious effects that excessive calcium hydroxide has on cell viability may be further decreased by partial substitution of the calcium hydroxide with magnesium hydroxide. However, calcium hydroxide may be a critical component for gelation and the inclusion of magnesium in excess may decrease gelation.

Calcium salts, such as hydroxyapatite, tri-calcium phosphate or combinations of the two, may also be included in the composition of the hydrogel. The calcium salts may strengthen the structural properties of the hydrogel and may further act as a ready reserve source of calcium and phosphate for the mineralized matrix synthesis performed by the mineralizing connective tissue cells. The adhesion and proliferation of connective tissue cells to the hydrogel may be further enhanced by the inclusion of other trace minerals such as zinc.

The hydrogel may be produced in a variety of different forms depending on the intended use of the hydrogel material. For example, porous, interconnected particles or thin, sandwiched sheets of hydrogel material may be used to induce bone regeneration, to fill periodontal pockets around a tooth caused by periodontal disease, or to fill large bone deficits caused by either cancer or traumatic injury. A less porous hydrogel material may be used as a direct pulp-capping agent within a tooth pulp chamber to promote dentin formation or to form a seal between the central pulp chamber and the roots of a young tooth in order to facilitate the formation of open apical root ends into mature, fully formed, tooth roots. In a less viscous form, the hydrogel may be applied to the outer root surface or to a deep cavity preparation, to serve as a dentin sealant.

One or more growth factors or antibodies to mineralizing tissue inhibitors may be incorporated into the composition of the hydrogel in order to stimulate the in-growth and proliferation of connective tissue stem cells within the hydrogel. Further, embryonic stem cells or adult stem cells derived from human fat, teeth or bone tissues may be seeded within the hydrogel in order to produce an engineered tissue in vitro or implanted for in vivo development and integration into adjacent connective tissue.

Specific ingredients included in the various aspects of the hydrogel composition are described in detail below.

a. Albumin

Serum albumin represents about 50% of circulating blood proteins and is a major component of the extracellular fluid that bathes all cells, including but not limited to osteocytes, odontoblasts, dentinal tubules, and other cells of the pulp. Albumin is a typical component of demineralized and electrophoretically separated dentin matrix proteins. Decreases in circulating albumin have been correlated with an increased incidence of root caries; minor injuries of the oral tissues are known to increase the amount of albumin pooling within the injured area. Albumin circulates through the bone matrix and is incorporated into bone due to the binding of albumin to the mineralizing surface during bone formation.

The albumin may be included in the hydrogel as an aqueous solution. In particular, the albumin may be suspended in any known solvent, including but not limited to water, saline solution, and biological buffered solutions such as phosphate-buffered saline solution. In one aspect, the albumin may be provided as an aqueous solution in an amount ranging from about 7% to about 50% (w/v). In a preferred aspect, the albumin is provided as an about 30% (w/v) solution of serum albumin in phosphate-buffered saline solution.

Albumin is a critical component of the hydrogel composition that is necessary for the gelling of the hydrogel once the albumin solution is combined with the suspension of calcium salts. For example, if an albumin solution containing less than about 7% (w/v) of albumin is combined with suspension of calcium salts in a volume ratio of less than about 1.0:2.5 (albumin: calcium salt), the hydrogel may not form.

b. Fibrinogen

Although mineralizing connective tissue cells will grow and migrate over the surface of a hydrogel scaffolding made up of albumin and calcium salts, these cells do not generally adhere well to the hydrogel. Without being limited to any particular theory, the cell adhesion may not occur because there are no known connective tissue cell-binding sites on albumin. To enhance cell adhesion, other molecules, such as fibrinogen, may be included within the hydrogel bioscaffold composition to provide multiple cell-binding sites, thus rendering the hydrogel more amenable to cell adhesion.

Fibrinogen may also bind to the membrane integrins of mineralizing connective tissue cells or their stem cell precursors. Fibrinogen is a precursor form of fibrin, and the addition of thrombin and calcium to fibrinogen brings about its conversion to fibrin and the subsequent self-assembly of fibrin molecules to form a tacky network that aids in the clotting process. Fibrinogen and fibrin may bind to integrins located within mineralizing connective tissue cell membranes, using the RGD recognition sequence that comprises arginine, glycine, and aspartic acid, resulting in a strengthened and enlarged clot through the binding of additional cells or cell fragments such as platelets.

To improve the initial adhesion of cells to the hydrogel, fibrinogen at a concentration from about 0.01 mg/mL to about 1.0 mg/mL may be included in the albumin solution used to produce the hydrogel. In a preferred embodiment, fibrinogen at a concentration of about 1.0 mg/mL may be included in the albumin solution used to produce the hydrogel. The concentration of fibrinogen included in the hydrogel may govern the concentration of potential cell adhesion sites within the hydrogel. Upon dilution of the solution with calcium and/or magnesium salts, the final fibrinogen concentration in the hydrogel composition may vary from about 0.3 to about 0.5 mg/mL prior to gelling. This concentration range is much more dilute than the extremely high concentrations of fibrinogen (ranging from about 50 mg/mL to about 100 mg/mL) used in the labile hydrogel composition of fibrin glue, a product that is clearly not suited for use as a scaffold to support mineralized tissue growth.

In addition to providing adhesion sites for connective tissue cells, fibrinogen may influence the release of various chemokines related to connective tissue development. For example, platelet-derived growth factor (PDGF) may be bound to fibrinogen and included in the hydrogel, resulting in a slow, sustained release of PDGF from the hydrogel during use. PDGF is a key growth factor in platelets and is up-regulated in osteoblasts and odontoblasts during peak levels of type I collagen formation in bone and dentin issues. The release of other chemokines, such as vascular endothelial growth factor (VEGF) and fibroblastic growth factor-2 (FGF-2) by connective tissue stem cells may also be affected by the presence of fibrinogen that may be included in the hydrogel. In an aspect, chemokines including but not limited to PDGF, VEGF, FGF-2, and combinations thereof may be included in the hydrogel.

c. Antioxidants

One or more antioxidants may be included within the albumin solution used to produce the hydrogel in order to minimize harmful reactive oxygen species, to inhibit bacterial growth, and to provide other beneficial effects for the connective tissue cells within the hydrogel. Any known food-grade or pharmaceutical-grade antioxidant may be included in the albumin solution, including but not limited to ascorbic acid and its salts; acetylcysteines; tocopherols; tocotrienols; polyphenolic antioxidants such as resveratrol and flavenoids; carotenoids such as lycopene, carotenes and lutein; and glutathione.

N-acetylcysteine is known to stimulate the formation of the primary intracellular antioxidant glutathione. N-acetylcysteine, which boosts the total antioxidant titer both within cells and within the extracellular fluid, may decrease the generation of reactive oxygen species that are devastating to cell viability and the functional health of cells. N-acetylcysteine may also neutralize toxins given off by composite resins, stimulate reparative dentin formation, and prevent the formation of bacterial biofilms. N-acetylcysteine may be included in the albumin solution at a concentration ranging from about 10 mM to about 40 mM. In a preferred aspect, N-acetylcysteine may be included in the albumin solution at a concentration of about 40 mM.

The inclusion of N-acetylcysteine to a 30% albumin solution containing 1 mg/mL of fibrinogen may increase the rate of gelation of the resulting hydrogel in a dose-dependent manner. The working time of the hydrogel may be decreased by the addition of N-acetylcysteine within the albumin solution; the higher the concentration of N-acetylcysteine in the albumin solution, the shorter the working time of the hydrogel. N-acetylcysteine at a final concentration of 20 mM may result in the initiation of gelation in less than 1 minute. Working time is defined herein as the time elapsed between the initial mixing of the hydrogel ingredients and the curing of the hydrogel into a stiffened bioscaffold structure.

Ascorbic acid is a known antioxidant and cell protectant. In its 2-phosphoascorbic form, ascorbic acid may also function as a substrate for alkaline phosphatase, an enzyme intimately involved in the mineralization process. 2-phosphoascorbic acid may be included in the albumin solution in an amount ranging from about 10 µg/mL to about 100 µg/mL. In a preferred aspect, 2-phosphoascorbic acid may be included in the albumin solution in an amount ranging from about 25 µg/mL to about 50 µg/mL.

d. Calcium Compounds

Calcium compounds may be included in the hydrogel in the form of an aqueous suspension of calcium salts that may be mixed with the albumin solution to produce the hydrogel. The calcium salts, in particular calcium hydroxide, are a critical ingredient for the production of the hydrogel; the hydrogel may not form properly in the absence of calcium hydroxide. The calcium salts may further provide calcium ions for the formation of hydroxyapatite crystals in newly forming bone, dentin, and cementum during connective tissue repair. Non-limiting examples of calcium salts suitable for use in the aqueous suspension of calcium salts includes calcium hydroxide, hydroxyapatite, and tri-calcium phosphate.

Calcium hydroxide has at least several known applications in dental surgery. Calcium hydroxide has been used as a covering for a viable pulp, and may have an antibacterial function in this application due to its high pH. Calcium hydroxide has also been used as a mild dentin etchant; the etching of dentin using calcium hydroxide is known to release matrix-bound growth factors that stimulate dentin repair. Calcium hydroxide may also act as a source of calcium ions for the potential formation of hydroxyapatite crystals in newly forming bone, dentin and cementum during tissue repair.

Calcium hydroxide may be included in the hydrogel in the form of an aqueous suspension of calcium salts that includes calcium hydroxide particles suspended in water in an amount ranging from about 0.1 g of calcium hydroxide to about 1.0 g per 10 mL of water. In a preferred aspect, the aqueous solution includes calcium hydroxide particles suspended in water in the amount of about 0.5 g of calcium hydroxide per 10 mL of water. The amount of calcium salts included within the aqueous suspension of calcium salts may influence the working time of the hydrogel with the lower concentrations of calcium salts resulting in longer working times for the hydrogel.

The amount of calcium salts included within the hydrogel may also influence the rigidity of the cured hydrogel. Lower amounts of calcium salts result in a more flexible and elastic hydrogel when cured. Higher amounts of calcium salts result in a more rigid hydrogel when cured. Extremely high amounts of calcium salts degrade the structural integrity of the cured hydrogel, thereby resulting in a chalky cured hydrogel.

In addition to calcium hydroxide, other calcium salts such as hydroxyapatite or tri-calcium phosphate may be included with the calcium hydroxide in the suspension of calcium salts. Hydroxyapatite, tri-calcium phosphate, or a combination of hydroxyapatite and tri-calcium phosphate may be added to the calcium hydroxide in the aqueous suspension of calcium salts in an amount ranging from about 0.02 g to about 0.2 g per 10 mL of water. In a preferred aspect, hydroxyapatite, tri-calcium phosphate, or a combination of hydroxyapatite and tri-calcium phosphate may be added to the calcium hydroxide in the aqueous suspension of calcium salts in an amount ranging from about 0.05 g to about 0.1 g per 10 mL of water. Higher amounts of hydroxyapatite and/or tri-calcium phosphate in the suspension of calcium salts may result in a degraded, chalky hydrogel.

In another aspect, a saturated aqueous suspension of calcium hydroxide may be added to the albumin solution at a volume ratio ranging from about 1:1 to about 1:2.5 (calcium hydroxide suspension: albumin solution). The saturated aqueous suspension of calcium hydroxide may include at least 15 mg of calcium hydroxide per 10 mL of water. In this aspect, a thin, precipitated hydrogel film or thin hydrogel layer forms. When cured, the thin hydrogel layers may be used for a variety of applications including but not limited to sealants, adhesive substrates for cell attachment, and coatings for tooth or bone implants. Such formulations may also be useful as additives to currently employed dentin bonding agents and pulp capping agents in order to render them more user-friendly and to decrease the tissue toxicity of these products.

e. Magnesium Hydroxide

The hydrogel may further include other known ionic metal compounds including but not limited to magnesium and zinc ions. Magnesium and zinc are known coenzymes for alkaline phosphatase, an enzyme known to be critical for the initiation of mineralization in connective tissues. The ionic metal compounds may be provided in any known form including but not limited to chelates, acetates, aspartates, citrates, glucoheptonates, gluconates, glycerates, picolinates, monomethionines, and sulfates. Magnesium ions may be included in the albumin solution in an amount up to about 2 mM, and zinc ions may be included in an amount up to about 0.5 mM.

In addition to its coenzyme function, the magnesium ions may further contribute to the viability of any connective tissue stem cells adhered within the hydrogel. Typical connective tissue cells actively regulate the concentration of magnesium and calcium ions within the cytoplasm such that calcium ions are ejected into the extracellular fluid and magnesium ions are moved from the extracellular fluid into the cytoplasm. As a result, the connective tissue cells typically maintain a higher intracellular concentration of magnesium ions and a lower intracellular concentration of calcium ions relative to the corresponding extracellular concentrations. Without being bound to any particular theory, the inclusion of magnesium ions in the hydrogel may provide a less stressful environment for adhered connective tissue cells due to the more favorable concentration gradient of magnesium, thus enhancing cell viability.

In an aspect, calcium hydroxide in the aqueous suspension of calcium salts may be partially replaced by magnesium hydroxide. In this aspect, the mass ratio of calcium hydroxide to magnesium hydroxide in the aqueous suspension of magnesium and calcium salts may range from about 2.5:1 to about 6:1.

In a preferred aspect, the mass ratio of calcium hydroxide to magnesium hydroxide in the aqueous suspension of calcium salts may be about 2.5:1. When magnesium hydroxide is partially substituted for calcium hydroxide at this mass ratio in the aqueous suspension of calcium salts used to produce the hydrogel, it was discovered unexpectedly that the resulting cured hydrogel was highly flexible compared with hydrogels formed using comparable amounts of calcium hydroxide alone. Thus, the amount of magnesium hydroxide included in the hydrogel may be varied to control the flexibility of the resulting cured hydrogel. Further, the higher the concentration of magnesium relative to calcium, the longer the time required for gelation to occur in a composition that also includes albumin, fibrinogen, and N-acetylcysteine at the concentrations described above. p f. Beta-Glycerol Phosphate and Zinc To enhance differentiation and to provide adequate organic phosphate for the enzyme alkaline phosphatase in the initiation of mineralization of the mineralizing connective tissue cells on the hydrogel scaffolding, beta-glycerol phosphate may be added at a concentration from about 10 mM to about 20 mM. In a preferred aspect, 10 mM beta-glycerol phosphate is added to the albumin/fibrinogen/ascorbic acid solution. Upon dilution with calcium/magnesium salts, the concentration in the final composition may vary from about 2.0 mM to about 5.0 mM.

Zinc and magnesium are coenzymes for alkaline phosphatase. In a preferred aspect, zinc at a concentration of about 0.2 to about 0.35 mM may be added to enhance and stabilize the effects of the alkaline phosphatase within developing mineralizing repair tissue.

II. Method of Producing the Hydrogel

The hydrogel may be produced by combining and mixing together the albumin solution and the aqueous suspension of calcium salts or combination of calcium and magnesium salts. When combined, the mixture undergoes an exothermic reaction to form the hydrogel, which may set within in a working time ranging between about 30 seconds to about 10 minutes.

The albumin solution may include additional ingredients as described above, including, but not limited to, fibrinogen, antioxidants, alkaline phosphatase substrates, metal ions, and chemokines. The aqueous suspension of calcium salts may include calcium hydroxide and magnesium hydroxide as well as hydroxyapatite and/or tri-calcium phosphate.

At the upper concentrations of those additives tested, the relative concentrations of albumin, N-acetylcysteine, calcium hydroxide, and magnesium hydroxide in the final mixture affect the working time for the initiation of gelation in an interdependent manner. For example, when the composition includes albumin at 15% (w/v) concentration and 10 mM of N-acetylcysteine, the partial substitution of magnesium hydroxide for calcium hydroxide slows the gelation time of the final composition. Likewise, if either the albumin or N-acetylcysteine concentration is reduced again by half with a calcium hydroxide solution, the gelation time increases. In a preferred aspect, a solution that includes 30% (w/v) concentration of albumin and 40 mM N-acetylcysteine is mixed at a volume ratio of 1:1 with a mixed suspension of magnesium hydroxide and calcium hydroxide in a molar ratio of 2.5:1 (calcium hydroxide: magnesium hydroxide). The working time for the initiation of gelation is about 1 minute for this composite mixture. Variation of the molar ratio of the magnesium/calcium suspensions may result in lengthening or shortening the working times of the hydrogels. The ratios of ingredients included in the hydrogel may be varied in order to enhance the tensile strength of the hydrogel. The inclusion of beta-glycerol phosphate, 2-phosphoascorbic acid, and zinc in this preferred aspect appear to have minimal effect on the working times or tensile strength of the hydrogel.

Any known technique of mixing and applying the hydrogel may be used in various aspects. The hydrogel may be produced by combining the albumin solution and the calcium/magnesium salt suspension in a container and constant stirring. In another aspect, the hydrogel may be produced by drawing the albumin solution and the calcium salt suspension in a syringe barrel and mixing the mixture using known methods, including, but not limited to, shaking or agitation.

In other aspects, the hydrogel may be seeded with embryonic stem cells or adult stem cells derived from human fat, teeth, or bone tissues. In these aspects, the hydrogel may further incorporate compounds known to contribute to the survival and proliferation of the stem cells, such as cell nutrients and growth factors.

The introduction of a fluid such as water or a buffer solution to the freshly set gel may induce moderate expansion of the gel. Although the pH of the gel is initially alkaline due to the inclusion of the calcium hydroxide and/or magnesium hydroxide, the pH of the set hydrogel may be reduced by one or more rinses in water or buffer solution. Once set, the hydrogel is a relatively stable compound that is resistant to dissolving, even in concentrated hydrochloric acid. The hydrogel may be dried and then reconstituted by rehydration with water or buffer solution.

Figure 1:
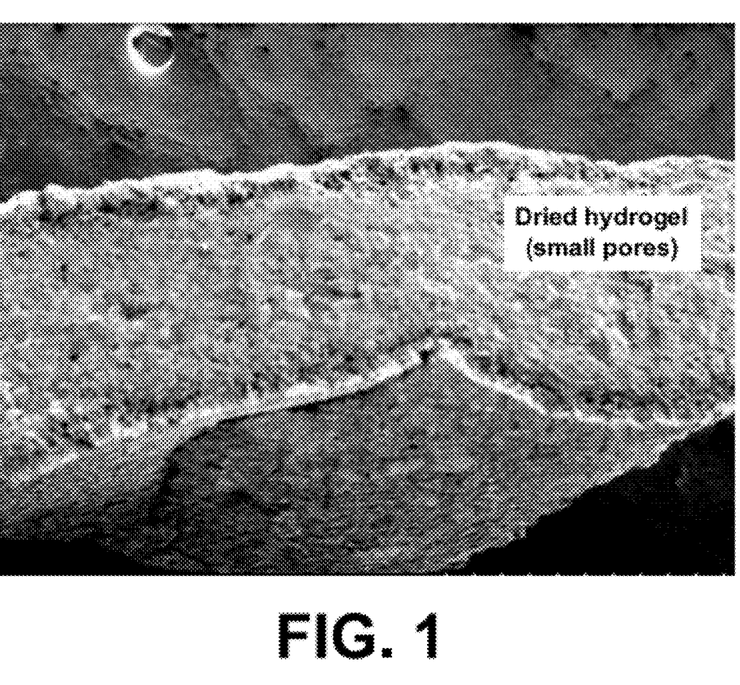
FIG. 1 is a scanning electron microscope image of a dried hydrogel with very low porosity.
Figure 2:
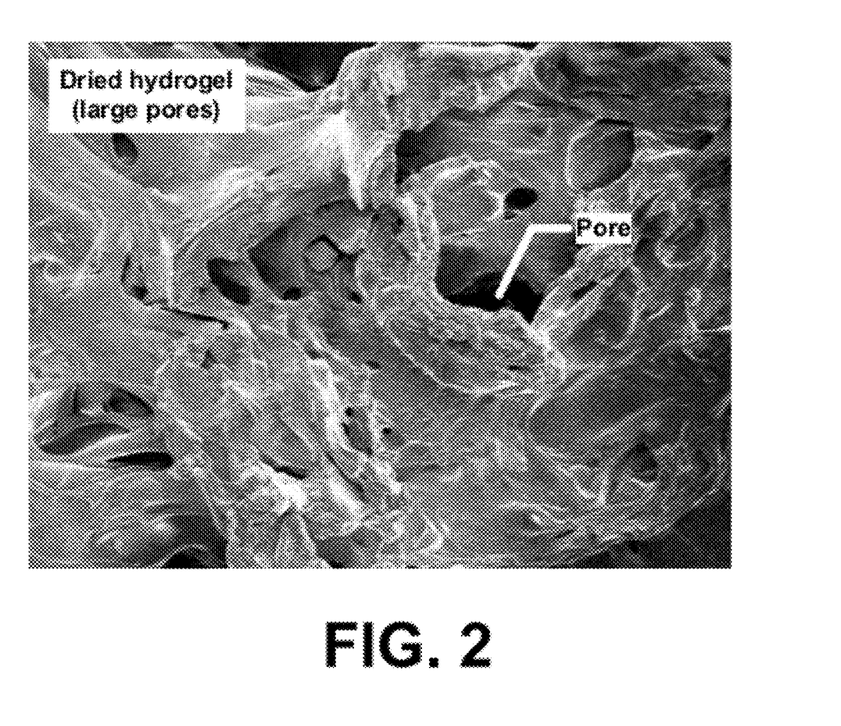
FIG. 2 is a scanning electron microscope image of a dried hydrogel with intermediate-sized pores.
Figure 3:
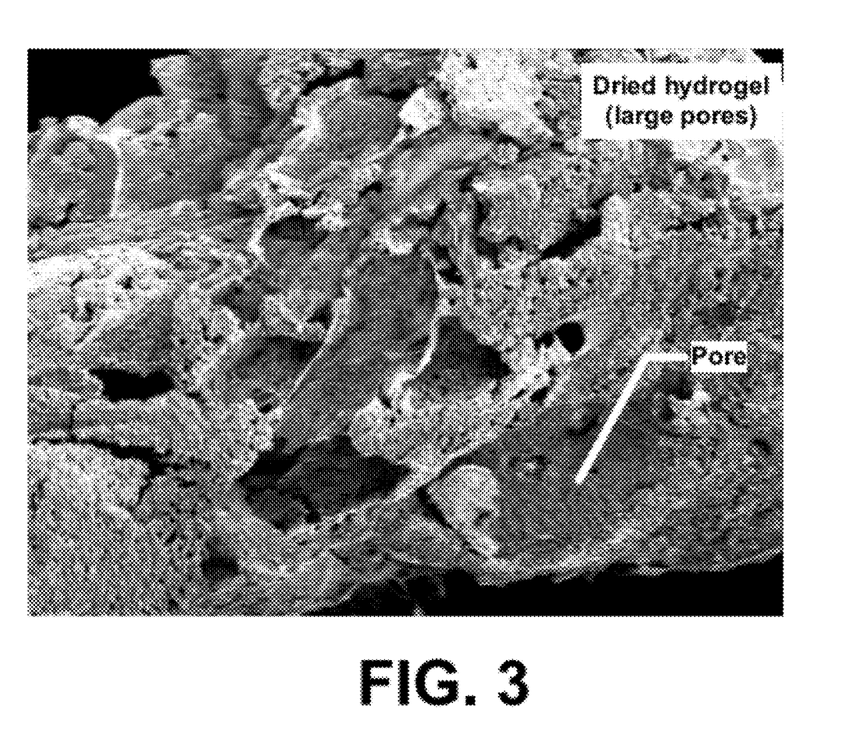
FIG. 3 is a scanning electron microscope image of a dried hydrogel with large pores.

Pores may be formed within the hydrogel by introducing a gas within the uncured hydrogel during the production of the hydrogel. For example, a gas may be introduced into the hydrogel mixture by any known method during mixing, including vigorous stirring and the introduction of bubbles using a compressed gas source. Depending on the amount of gas introduced during mixing, the consistency of the hydrogel may range from a relatively solid hydrogel material, as shown in FIG. 1, to a porous hydrogel, as shown in FIG. 2 and FIG. 3. The pores within the hydrogel may range in diameter from about 100 microns to about 3,000 microns, depending upon the amount and speed in which the gas is introduced. For example, slow stirring may result in an essentially solid hydrogel material with very small pores, similar to the hydrogel shown in FIG. 1.

Any suitable gas may be introduced into the hydrogel, including but not limited to air, oxygen, nitrogen, and carbon dioxide. The composition of the gas introduced into the hydrogel may result in the incorporation of at least a portion of the gas compound into the hydrogel material, which may influence the properties of the hydrogel such as biocompatibility or rigidity. In an aspect, carbon dioxide gas may be introduced during the mixing of the hydrogel ingredients, resulting in the inclusion of an amount of carbon into the hydrogel. The carbon may enhance the development of bone tissue, which is known to include higher proportions of carbonate substitution within the hydroxyapatite formed during early bone development compared to later stages of bone development. When pores are desired within the cured hydrogel, the freshly formed gel may be placed under vacuum until the gel is fully set to guard against the potential collapse of the pores within the hydrogel.

In another aspect, when the magnesium-to-calcium ratio in the gel is greater than 3:1, gelation is decreased, such that a tacky, pliable liquid results. This more liquid version of the hydrogel may be used as a coating to promote osseointegration around bone and tooth implants or as a sealant for open dentinal tubules on either the inside surfaces of the tooth such as within the pulp chamber, or on the outside surfaces of the tooth, such as the crown or root dentin.

EXAMPLES

The following examples illustrate various aspects of the invention.

Example 1

Bioresorbability of Hydrogel

To assess the biocompatibility and resorption properties of the hydrogel, the following experiment was conducted. A hydrogel was produced using the methods described above that included 30% (w/v) of serum albumin in phosphate buffer and a 1:20 (w/v) suspension of calcium hydroxide in water. A sample of the hydrogel was encapsulated to form an implant. The implant was surgically placed into the thigh of a rat together with a venous blood supply. The implant was removed about 6 weeks after implantation and analyzed to compare the composition of the hydrogel after 6 weeks of implantation with the hydrogel prior to implantation. The results of this experiment indicated that the hydrogel was totally resorbed within 6 weeks of implantation.

Example 2

Bone Tissue Formation Using Hydrogel Support

To assess the capability of the hydrogel to act as a support or scaffold for bone repair processes, the following experiment was conducted. A fetal calf bone cell culture model was used to assess the efficacy of the hydrogel as a support for developing bone tissue during the growth and repair of fetal calf bone tissues.

Figure 4:
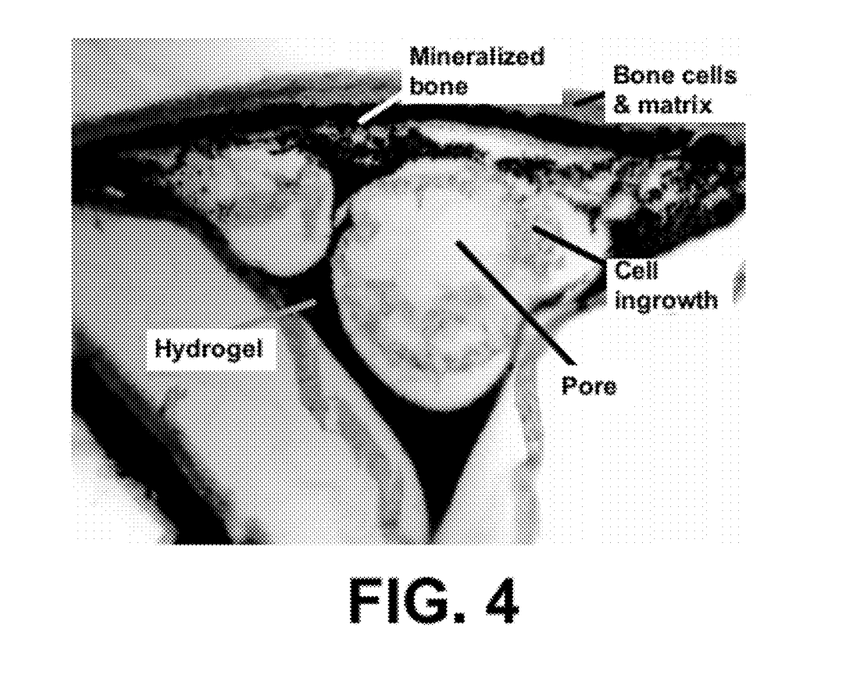
FIG. 4 is a conventional light microscope image of a fresh-frozen and stained histological cross-section of a sheet of fetal calf bone cultured from bone stem cells using a hydrogel as a bioscaffold.
Figure 5:
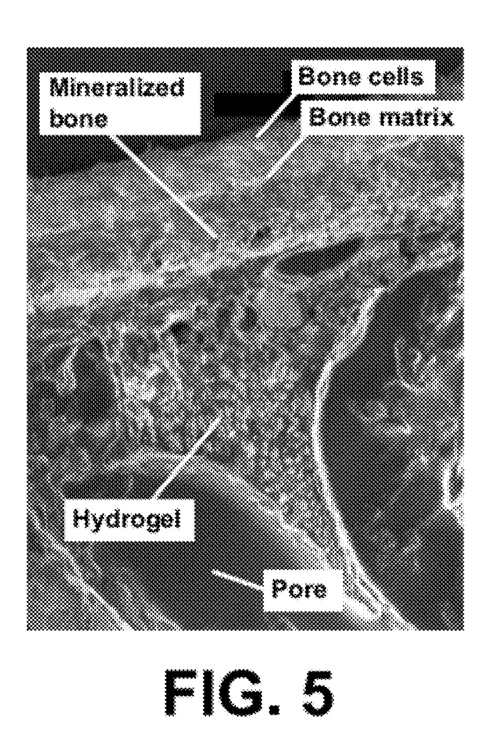
FIG. 5 is a scanning electron microscope image of a repair of a fetal calf bone culture growing on a hydrogel bioscaffold.
Figure 6:
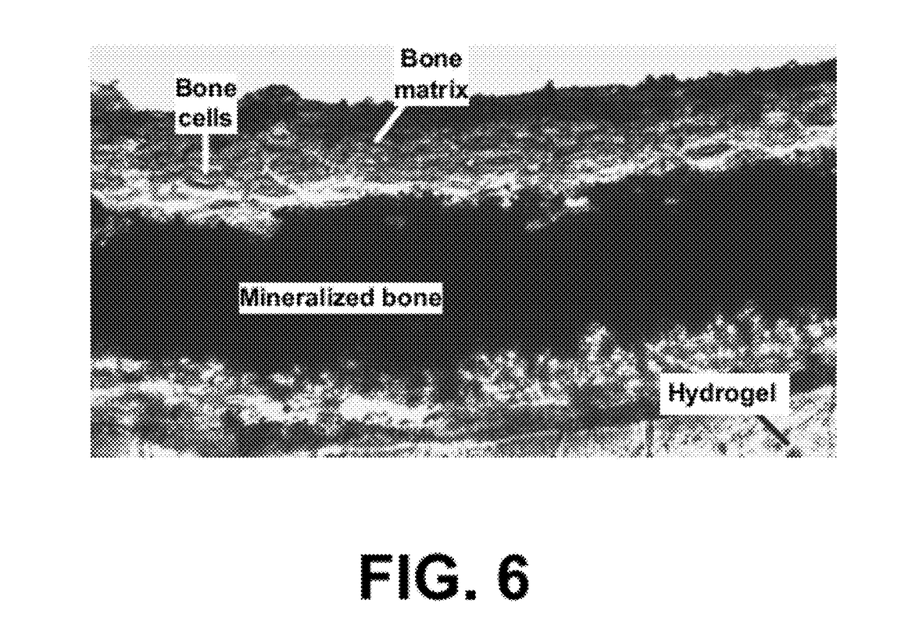
FIG. 6 is a high-power light microscope image of a fresh-frozen, stained histological cross-section of cultured fetal calf bone grown on a hydrogel bioscaffold.

A solution containing albumin, fibrinogen and N-acetylcysteine was mixed with calcium hydroxide to form a hydrogel solution. Separate batches were applied to plastic coverslips in 24-well culture dishes. Some coverslips were left untreated as controls. The first-passage fetal calf bone cell precursors were seeded at about 200,000 cells/well and grown to confluence. The cultures were stimulated to produce bone for up to 21 days. The cultures were preserved and frozen. Histological sections were obtained and visualized using conventional light microscopy and scanning electron microscopy. FIG. 4 is a conventional light microscope image of a frozen and stained histological cross-section of the bone tissue, showing the porous hydrogel scaffold supporting an overlying mineralized bone matrix and a multilayer of overlying bone cells. FIG. 5 is a scanning electron microscope image of a section of the cultured fetal calf bone, showing the bone tissue overlying the hydrogel bioscaffold. FIG. 6 is a high-power light microscope image of a histological section of the fetal calf bone tissue in which the mineralized bone matrix was stained black using silver nitrate, the overlying bone cells was stained blue, and the unmineralized bone matrix was stained red. The hydrogel in FIG. 6, situated along the lower edge of the image, acted as a support for the growing bone tissue. In all images, mineralized bone matrix with overlying live bone cells and unmineralized bone matrix was supported by the implanted hydrogel, indicating that the hydrogel implant was biocompatible with the surrounding bone tissue and facilitated the repair and growth of replacement bone tissue.

The results of this experiment demonstrated the efficacy of the hydrogel as a support for developing bone tissue in vivo.

Example 3

Tubular Dentin Formation on Hydrogel

To assess the capability of the hydrogel to act as a support or scaffold for dentin repair processes, the following experiment was conducted. A human dental pulp stem cell culture model was used to assess the efficacy of the hydrogel as a support for developing dentin during the growth and repair of tooth tissues.

Human dental pulp stem cells that were grown and seeded on a hydrogel scaffolding in a manner similar to that described in Example 2. First-passage cells were stimulated to differentiate by the use of one combination of growth factors, then stimulated to produce dentin matrix by applying a second group of growth factors in the nutrient medium. After 14 days of culture, the cultures were preserved and frozen. Histological sections were obtained and visualized using conventional light microscopy and scanning electron microscopy.

Figure 7:
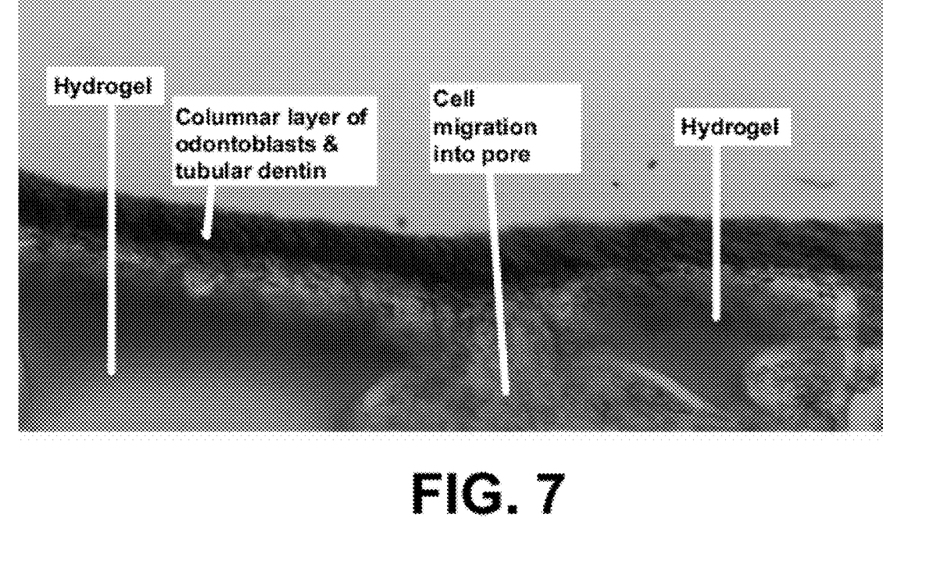
FIG. 7 is a photograph of cultured odontoblasts derived from human dental pulp stem cells in the process of forming tubular dentin on a hydrogel bioscaffold.

FIG. 7 shows a microscopic image of the human dental pulp stem cells cultured on the hydrogel. The image showed that the stem cells successfully formed a single, columnar layer of odontoblast cells and that tubular dentin had begun to form. The results of this experiment demonstrated that human dental pulp stem cells may form the uniform, single layer of mineralizing connective tissue cells unique to dentin on a hydrogel bioscaffold.

Example 4

Stimulation of Bone Formation in the Rat Mandibular Defect Model

To assess the capability of the hydrogel to stimulate bone repair processes, the following experiment was conducted. An in vivo rat mandibular defect model was used to assess the efficacy of the hydrogel as a bone repair stimulant during the growth and repair of bone tissues.

Defects (2 mm×3 mm×1 mm) were surgically produced on both sides of the body of the mandible of anesthetized rats. The defects were centered on the first molars. The defect on one side was filled with hydrogel; the defect on the other side of the mandible was allowed to heal normally for up to 28 days.

To produce the hydrogel, 0.15 mL of a solution containing 30% (w/v) albumin, 0.1 mg/ML fibrinogen, 40 mM N-acetylcysteine, 10 mM beta-glycerol phosphate, and 50 µg/mL phosphoascorbic acid was mixed 1:1 in a 3-mL syringe with 0.15 mL of a suspension of calcium hydroxide made from a 1:20 w/v calcium hydroxide powder and water. Within 15 seconds after vigorous shaking, the final volume of 0.3 mL was injected into the defect. The hydrogel formed in the defect within 1 minute.

Twenty-eight days postsurgery, the rats were sacrificed and the mandibular bone tissues removed from the surgically produced defects were compared using both three-dimensional image reconstruction (micro-computed tomography; micro-CT) and conventional histology of demineralized cryostat sections. These examinations indicated that the inclusion of the hydrogel within the surgically-produced defect resulted in an increase in the rate of bone repair over the 28-day period relative to tissue from control rats in which the defects were not filled with the hydrogel.

It should be understood from the foregoing that, while particular embodiments have been illustrated and described, various modifications can be made thereto without departing from the spirit and scope of the invention, as will be apparent to those skilled in the art. Such changes and modifications are within the scope and teachings of this invention, as defined in the claims appended hereto.

What is claimed is:

1. A hydrogel composition for use as a support scaffold for developing mineralizing connective tissue, the composition comprising:
   an albumin solution comprising about 30% (w/v) of albumin in a phosphate buffer and N-acetylcysteine in an amount ranging from about 10 mM to about 40 mM; and
   an aqueous suspension comprising about 0.5 mg of calcium hydroxide per 10 mL of water;
   wherein the ratio of the albumin solution volume and the aqueous suspension of calcium hydroxide ranges from about 1:1 to about 1:2.5.

2. The composition of claim 1, wherein the albumin solution further comprises fibrinogen in an amount ranging from about 0.01 mg/mL to about 1.0 mg/mL.

3. The composition of claim 1, wherein the albumin solution further comprises 2-phosphoascorbic acid in an amount ranging from about 25 µg/mL to about 50 µg/mL 4. The composition of claim 1, further comprising beta-glycerol phosphate in an amount of about 2 mM to about 5 mM.

5. The composition of claim 1, further comprising zinc ions in an amount of about 0.2 mM to about 0.35 mM.

6. The composition of claim 1, wherein the aqueous suspension further includes the partial substitution of an aqueous suspension of magnesium hydroxide for calcium hydroxide, wherein the mass ratio of the calcium hydroxide to magnesium hydroxide is about 2.5:1 to about 6:1 and the total volume ratio of the aqueous suspension to albumin solution is about 1:1.

7. The composition of claim 1, wherein the aqueous suspension further comprises at least one additional calcium salt chosen from hydroxyapatite and tri-calcium phosphate in an amount of about 0.02 g to about 0.2 g per 10 mL of water.

8. The composition of claim 1, further comprising stem cells chosen from embryonic stem cells and adult stem cells, wherein the stem cells are seeded throughout the hydrogel composition.

9. The composition of claim 1, wherein a plurality of pores comprising pore diameters ranging from about 100 microns to about 3,000 microns are contained within the composition.

10. A hydrogel composition for use as a coating for a bone or tooth implant, the composition comprising:
 an albumin solution comprising about 30% (w/v) of albumin in a phosphate buffer, N-acetylcysteine in an amount ranging from about 10 mM to about 40 mM, and fibrinogen in an amount ranging from about 0.1 mg/mL to about 1.0 mg/mL; and,
 an aqueous suspension comprising about 0.5 mg of calcium hydroxide per 10 mL of water;
wherein the ratio of the albumin solution volume and the aqueous suspension volume of calcium hydroxide ranges from about 1:1 to about 1:2.5 and wherein the composition promotes osseointegration around a coated bone or tooth implant.

11. The composition of claim 10, further comprising any one or more of the following:
 2-phosphoascorbic acid in an amount ranging from about 25 µg/mL to about 50 µg/mL in the albumin solution;
 beta-glycerol phosphate in an amount of about 2 mM to about 5 mM in the composition; and
 zinc ions in an amount of about 0.2 mM to about 0.35 mM in the composition.

12. The composition of claim 1, wherein the aqueous suspension further comprises at least one additional calcium salt chosen from hydroxyapatite and tri-calcium phosphate in an amount of about 0.02 g to about 0.2 g per 10 mL of water.

13. A hydrogel composition for use as a sealant for exposed dentin, the composition comprising:
 an albumin solution comprising about 30% (w/v) of albumin in a phosphate buffer, N-acetylcysteine in an amount ranging from about 10 mM to about 40 mM, and 2-phosphoascorbic acid in an amount ranging from about 25 µg/mL to about 50 µg/mL ; and,
 an aqueous suspension comprising about 0.5 mg of calcium hydroxide per 10 mL of water;
wherein the ratio of the albumin solution volume and the aqueous suspension volume of calcium hydroxide ranges from about 1:1 to about 1:2.5 and wherein the composition inhibits bacterial growth on a sealed dentin surface.

14. The composition of claim 13, wherein the albumin solution further comprises at least one antioxidant chosen from a tocopherol, a tocotrienol, a polyphenolic antioxidant, and a carotenoid.

15. A method of producing a hydrogel composition for use as a support scaffold for developing mineralizing connective tissue comprising mixing an albumin solution and an aqueous suspension at a ratio from 1:1 to about 1:2.5 albumin solution: aqueous suspension, wherein:
 the albumin solution comprises about 30% (w/v) of albumin in a phosphate buffer, and, N-acetylcysteine in an amount ranging from about 10 mM to about 40 mM, and,
 the aqueous suspension comprises about 0.5 mg of calcium hydroxide per 10 mL of water.

16. The method of claim 15, wherein the working time of the composition ranges from about 30 seconds to about 10 minutes.

17. The method of claim 15, wherein the aqueous suspension further comprises at least one additional calcium salt to increase the hardness of the hydrogel, wherein the at least one additional calcium salt is chosen from hydroxyapatite and tri-calcium phosphate in an amount of about 0.02 g to about 0.2 g per 10 mL of water.

18. The method of claim 15, wherein a gas chosen from air, oxygen, nitrogen, carbon dioxide, and any combination thereof may be introduced into the hydrogel during or after mixing to introduce a plurality of pores ranging in diameter from about 100 microns to about 3,000 microns into the hydrogel.

\* \* \* \* \*